United States Patent [19]
Sugita et al.

[11] Patent Number: 5,637,612
[45] Date of Patent: Jun. 10, 1997

[54] ORAL ANTIBACTERIAL COMPOSITIONS AND METHOD FOR THE IMPROVEMENT OF GASTROINTESTINAL ABSORPTION OF PENEM OR CARBAPENEM ANTIBIOTICS

[75] Inventors: Osamu Sugita, Tatebayashi; Yasushi Kanai; Takumi Kojima, both of Ashikaga, all of Japan

[73] Assignee: Suntory Limited, Osaka, Japan

[21] Appl. No.: 425,223

[22] Filed: Apr. 18, 1995

Related U.S. Application Data

[60] Continuation of Ser. No. 258,218, Jun. 10, 1994, abandoned, which is a division of Ser. No. 828,571, Jan. 31, 1992, Pat. No. 5,354,748.

[30] Foreign Application Priority Data

| Feb. 1, 1991 | [JP] | Japan | 3-031475 |
| Feb. 1, 1991 | [JP] | Japan | 3-031476 |
| Feb. 1, 1991 | [JP] | Japan | 3-031477 |
| Feb. 1, 1991 | [JP] | Japan | 3-031478 |

[51] Int. Cl.$^6$ .......... A01N 37/00; A01N 37/02; A61K 31/215; A61K 31/22
[52] U.S. Cl. .......... 514/529; 514/546
[58] Field of Search .......... 514/529, 546

[56] References Cited

U.S. PATENT DOCUMENTS 4,539,208  9/1985  Kahan et al. .......... 514/195

Primary Examiner—Nathan M. Nutter
Attorney, Agent, or Firm—Oblon, Spivak, McClelland, Maier & Neustadt, P.C.

[57] ABSTRACT

Oral antibacterial compositions contain a penem or carbapenem antibiotic in combination with an absorption improver selected from substances capable of inhibiting the dipeptidase localized on/in epithelial cells of the small intestine, cilastatin, glutathione and N-acetyl-L-cysteine. Gastrointestinal absorption of the penem or carbapenem antibiotic can be improved by orally administering the absorption improver in combination with the antibiotic.

5 Claims, 1 Drawing Sheet

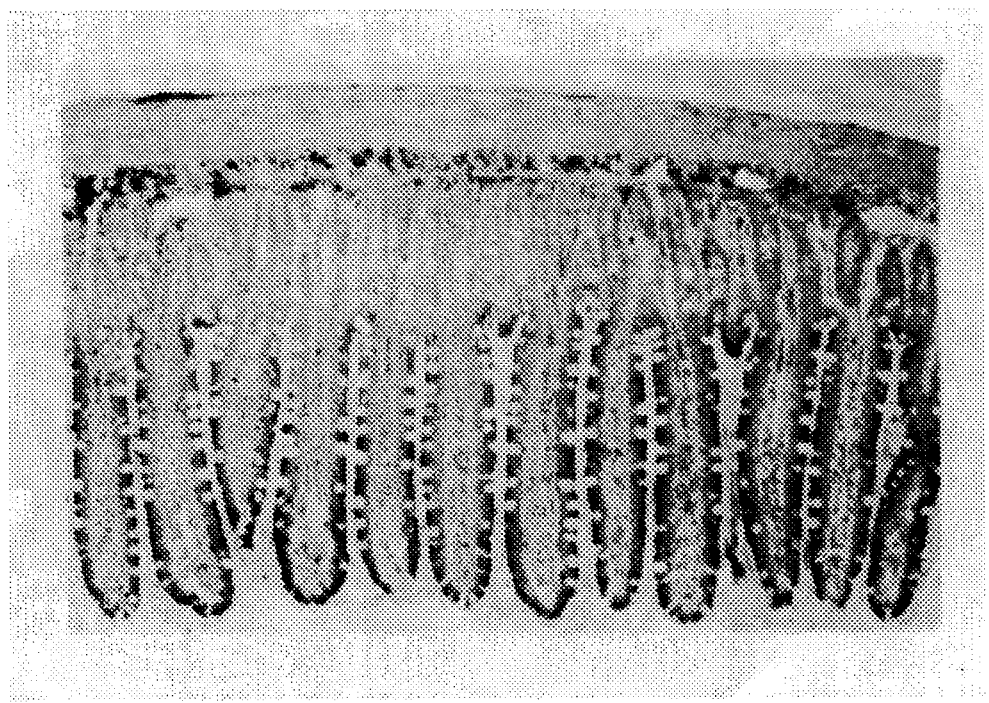

ORAL ANTIBACTERIAL COMPOSITIONS AND METHOD FOR THE IMPROVEMENT OF GASTROINTESTINAL ABSORPTION OF PENEM OR CARBAPENEM ANTIBIOTICS

This application is a continuation of application Ser. No. 08/258,218, filed on Jun. 10, 1994, now abandoned, which is a divisional of application Ser. No. 07/828,571, filed on Jan. 31, 1992 now U.S. Pat. No. 5,354,748.

BACKGROUND OF THE INVENTION

1) Field of the Invention

This invention relates to oral antibacterial compositions of penem or carbapenem antibiotics (hereinafter called "penems") with improved gastrointestinal absorption and also to a method for the improvement of gastrointestinal absorption of penems. More specifically, the present invention is concerned with oral antibacterial compositions with improved gastrointestinal absorption of penems and a method for the improvement of gastrointestinal absorption of penems, said compositions and method making use of a substance such as an inhibitor for the dipeptidase localized on/in epithelial cells of the small intestine.

2) Description of the Related Art

Active development of penems is now under way as new generation antibiotics succeeding penicillin and cephalosporin for their broad antibacterial spectrum and high levels of antibacterial activities.

However, actually the effective administration route of carbapenem antibiotics is only intravenous injection, because the carbapenem compounds are practically unabsorbable through the digestive tract.

On the other hand, it has been reported with respect to penem antibiotics that—paying attention to the fact that the kidney is a primary site of metabolism for penem antibiotics—penem antibiotics were administered in combination with a chemical substance capable of selectively inhibiting the enzyme, the β-lactam hydrolase, dipeptidase (E.C.3.4.13.11), localized in the kidney (hereinafter called "the renal dipeptidase inhibitor") (U.S. Pat. No. 4539208). As a method for using a renal dipeptidase inhibitor in combination with penem antibiotics, this U.S. patent discloses that the penem antibiotics and the renal dipeptidase inhibitor can be administered either in the form of a pharmaceutical composition containing these two compounds or be separately administered orally, intramuscularly or intravenously. The U.S. patent contains examples of the combined use, in which penems were administered orally. The method and dosage of the administration of the renal dipeptidase inhibitor, the resulting penem concentrations in plasma, etc. are, however, not satisfactory. Needless to say, the above patent does not suggest any improvement in gastrointestinal absorption.

Under the present circumstances as described above, it is very important for the expansion of the application field of the penems to find out a method to improve their gastrointestinal absorption so that sufficient therapeutic effects can be brought about by their oral administration. There is, therefore, an outstanding demand for the development of such an invention.

SUMMARY OF THE INVENTION

The present inventors have studied in detail the metabolism of orally-administered penems in the body. As a result, it has been found that the low absorption percentages of penems is attributed to their degradation by the dipeptidase-like enzyme localized on/in epithelial cells of the small intestine (hereinafter called "the dipeptidase derived from epithelial cells of the small intestine") and their gastrointestinal absorption can be improved by the oral administration of a substance capable of inhibiting the dipeptidase derived from epithelial cells of the small intestine (hereinafter may also be called "the intestinal dipeptidase inhibitor"), cilastatin, glutathione or N-acetyl-L-cysteine together with the penems. These findings have led to the completion of the present invention.

An object of this invention is, therefore, to provide an oral antibacterial composition which comprises an absorption improver selected from intestinal dipeptidase inhibitors, cilastatin, glutathione and N-acetyl-L-cysteine, and penems.

Another object of this invention is to provide a method for the improvement of the gastrointestinal absorption of penems, which comprises oral administration of the above absorption improver.

In one aspect of the present invention, there is thus provided an oral antibacterial composition comprising:
  an absorption improver selected from substances capable of inhibiting the dipeptidase localized on/in epithelial cells of the small intestine, cilastatin, glutathione and N-acetyl-L-cysteine; and
  a penem or carbapenem antibiotic.

In another aspect of the present invention, there is also provided a method for the improvement of the gastrointestinal absorption of a penem or carbapenem antibiotic, which comprises orally co-administering the said antibiotic and an absorption improver selected from substances capable of inhibiting the dipeptidase localized on/in epithelial cells of the small intestine, cilastatin, glutathione and N-acetyl-L-cysteine.

According to the oral antibacterial composition and oral absorption improving method of the present invention, the administration route for the penems can be broadened to oral administration although the administration route has been limited because they have been practically unabsorbable through the digestive tract.

Further, penems which have been slightly absorbed through the digestive tract can be increased in gastrointestinal absorption relative to their conventional absorption, whereby these penems are expected to achieve efficient therapeutic effects at a smaller dosage than their conventional dosage.

The present invention is, therefore, extremely important in broadening the application range or field of the penems.

BRIEF DESCRIPTION OF THE DRAWING

Photo 1 is a photomicrograph showing the development of localization of the dipeptidase in rat small intestine. Paraffin sections were prepared in a manner known per se in the art. Employed as a primary antibody was rabbit antiserum against the dipeptidase purified from the human kidney, as a secondary antibody antirabbit IgG goat IgG labeled with the peroxidase, and as a chromogenic substrate 3,3-diaminobenzidine.

As a result, it has been ascertained that the dipeptidase exists in the small intestine of a rat and the site of its localization is the epithelial brush-border membrane.

DESCRIPTION OF THE INVENTION AND PREFERRED EMBODIMENTS

As the intestinal dipeptidase inhibitors among the absorption improvers useful in the practice of the present invention, any intestinal dipeptidase inhibitors can be used insofar as they can inhibit the dipeptidase derived from epithelial cells of the small intestine and are not toxic to the body at their active concentrations.

Specific examples of the intestinal dipeptidase inhibitors include the compounds represented by any one of the following formulae (I)–(IV):

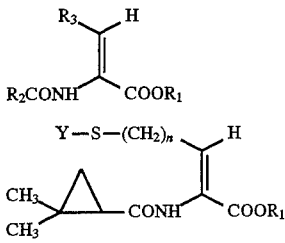

wherein $R_1$ represents a hydrogen atom, a $C_{1-6}$ lower alkyl or dialkylaminoalkyl group, or a pharmaceutically-acceptable cation, $R_2$ and $R_3$ represent $C_{3-10}$ and $C_{1-15}$ hydrocarbon groups, respectively, 1–6 hydrogen atoms of at least one of the hydrocarbon groups represented by $R_2$ and $R_3$ may be substituted by a like number of halogen atoms, one or more non-terminal methylene groups of at least one of the hydrocarbon groups represented by $R_2$ and $R_3$ may be substituted by a like number of oxygen or sulfur atoms, said sulfur atoms optionally being in an oxide form, one or more terminal hydrogen atoms of the hydrocarbon group represented by $R_3$ may be substituted by a like number of hydroxyl or thiol groups which may optionally be in an acylated or carbamoylated form, the amino group of said carbamoylated form optionally being a derivative such as acylamino, ureido, amidino, guanidino, or a quaternary-nitrogen-containing alkyl or substituted amino group or optionally being substituted by one or more acid groups such as carboxylic, phosphonic or sulfonic acid groups or esters thereof, amido groups or cyano groups, n is an integer of 3–5, and Y represents a hetero ring or phenyl group which may be substituted by one or more hydroxyl, oxo, carboxyl or methyl groups.

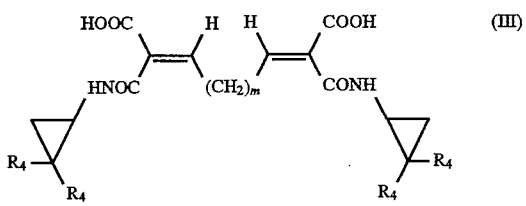

wherein m is an integer of 1–10 and $R_4$ represents a $C_{1-4}$ lower alkyl group or halogen atom.

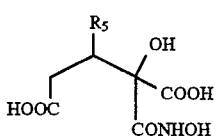

wherein $R_5$ represents a hydrogen atom or a lower alkyl or aryl group.

The above compounds can be their $C_{1-6}$ alkyl esters or pharmaceutically-usable salts and can be either racemic isomers or diastereomers.

Examples of the compound (I) or (II) among the compounds described above include Z-2-(2,2-dimethylcyclopropanecarboxamido)-8-trimethylammonium-2-octenoic acid, Z-2-(2,2-dimethylcyclopropanecarboxamido)-2-butenoic acid, Z-2- (2,2-dimethylcyclopropanecarboxamido)-2-pentenoic acid, Z-2-(2,2-dimethylcyclopropanecarboxamido)-2-octenoic acid, Z-2-(2,2-dimethylcyclopropanecarboxamido)-2-hexenoic acid, Z-8-[(carboxymethyl)methylamino]-2-(2,2-dimethylcyclopropanecarboxamido)-2-octenoic acid, Z-8-[(2-amino-2-oxoethyl)thio]-2-(2,2-dimethylcyclopropanecarboxamido)-2-octenoic acid, Z-2-(2,2-dimethylcyclopropanecarboxamido)-8-[1-(phosphono) ethylamino]-2-octenoic acid, Z-7-(L-amino-2-carboxyethylthio)-2-(2,2-dimethylcyclopropanecarboxamido)-2-heptenoic acid, Z-8-acetamido-2-(2,2-dimethylcyclopropanecarboxamido)-2-octenoic acid, Z-7-(3-hydroxy-2-pyridylthio)-2-(2,2-dimethylcyclopropanecarboxamido)-2-heptenoic acid, and Z-(3-carboxy-2-pyrydylthio)-2-(2,2-dimethylcyclopropanecarboxamido)-2-heptenoic acid.

Further, illustrative of the compound (III) include (Z,Z)-2,11-bis(2,2-dimethylcyclopropanecarboxamido)-2,10-dodecadienedione while examples of the compound (IV) include disodium 2-hydroxy-2-(hydroxycarbamoyl)-3-methylglutarate and disodium 2-hydroxy-2-(hydroxycarbamoyl)-3-phenylglutarate.

On the other hand, cilastatin, glutathione and N-acetyl-L-cysteine among the absorption improvers in the present invention are all compounds well known in the art and are readily available.

Of these, cilastatin and its salts have already been used in combination with thienamycin compounds such as imipenem (European Patent Publication No. 7614, etc.). As a preferred method in their use, parenteral administration of thienamycin compounds are disclosed. This is different from present invention in which cilastatin or its salt is orally administered together with the penems to significantly improve the biological availability of the penems.

It has also been reported with respect to a penem compound that, in the combination of cilastatin or its salt with the penem compound, these two compounds can be administered either in the form of a pharmaceutical composition comprising them or separately (U.S. Pat. No. 4,539,203). It is also disclosed in this U.S. patent that intravenous administration is preferred for the pharmaceutical composition containing these two compounds and, oral, intramuscular or intravenous administration is feasible as these compounds separately be administered.

Upon administration of penems with oral administration of cilastatin or its salt, penems are substantially ineffective when administered intravenously but can exhibit substantial effects only when administered orally. Accordingly, the invention of the above U.S. patent is clearly distinguished from the present invention.

Examples of penems whose absorption can be improved when combined with the absorption improver in accordance with this invention include compounds represented by the following formula (V):

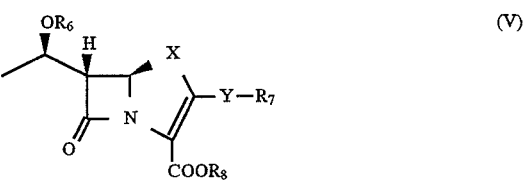

wherein $R_6$ represents a hydrogen atom or an OH-protecting group removable under physiological conditions, X represents —S— or —$CH_2$—, Y represents —S—, —$(CH_2)_l$—, l being an integer of 0–5, —O— or —N—, $R_7$ represents a hydrogen atom, an alkyl, aralkyl, aryl, hydroxyl, alkoxy, sulfido, amino, amido, carbonate or carbamate group, or a heterocyclic group containing 1–4 oxygen, sulfur or nitrogen atoms, and $R_8$ represents a hydrogen atom, a pharmacologically-acceptable alkali metal or a carboxyl-protecting group removable under physiological conditions.

Preferred examples of the above penems are those represented by the formula (V) in which $R_6$ represents a hydrogen atom, X represents —S—, Y represents —$(CH_2)_n$—, n being 0, $R_7$ represents a tetrahydrofuryl, tetrahydropyranyl, 1,4-dioxanyl, 5-oxo-oxolanyl, 2-oxo-1,3-dioxolany or 1,3-dioxolanyl group, and $R_8$ represents a hydrogen atom, a pharmacologically-acceptable alkali metal or a carboxyl-protecting group removable under physiological conditions; and those represented by the formula (V) in which $R_6$ represents a hydrogen atom, X represents —S—, Y represents —$(CH_2)_n$—, n being 1, and $R_7$ represents a 5— or 6-membered, cyclic heteroaliphatic group containing one or two oxygen atoms in the ring thereof.

Preparation of the oral antibacterial composition of this invention can be conducted by combining the absorption improvers with the penems at a suitable ratio and formulating for oral use in a manner known per se in the art.

When cilastatin or its salt is used as an absorption improver, the mixing ratio (molar ratio) of the penems to cilastatin or its salt is about 1:3 to about 2000:1, and preferably about 10:1 to about 300:1. When glutathione or its salt is used as an absorption improver, the mixing ratio (molar ratio) of the penems to glutathione or its salt is about 1:3 to about 110:1, and preferably 1.1:1 to 22:1. Further, when N-acetyl-L-cysteine or its salt is used as an absorption improver, the mixing ratio (molar ratio) of the penems to N-acetyl1-L-cysteine or its salt is about 1:3 to about 60:1, and preferably about 1:1 to about 10:1.

The antibacterial composition of the present invention can be formulated for oral use such as tablets, granules, powders, capsules, syrups or liquid preparations. Upon formulation of these dosage, pharmaceutically-acceptable carriers well known in the art can be used.

Examples of such carriers include carriers for solid preparations, for example, diluents such as lactose, sucrose, glucose, starch and crystalline cellulose, binders such as starch, hydroxypropylcellulose and carboxymethylcellulose, and lubricants such as talc, stearic acid and stearate salts; and carriers for liquid preparations, such as sucrose, glucose, fructose, invert sugar, sorbitol, xylitol, glycerin, gum arabic, tragacanth and carboxymethylcellulose sodium.

To practice the method of this invention for the improvement of gastrointestinal absorption of penems, it is only necessary to administer the absorption improver either concurrently with penems or after the administration of the penems.

The absorption improvers can be administered at any dosage insofar as it can inhibit the dipeptidase derived from intestinoepithelial cells without any toxicity to the body.

For the administration of the absorption improvers, it is convenient to use a gastrointestinal absorption improver preparation comprising in combination the absorption improvers and a pharmaceutically-acceptable carrier known in the art. This gastrointestinal absorption improver preparation can be in the form of an oral preparation such as tablets, granules, powders, capsules, syrups or liquid preparations.

Examples of usable pharmaceutically-acceptable carriers include carriers for solid preparations, for example, diluents such as lactose, sucrose, glucose, starch and crystalline cellulose, binders such as starch, hydroxypropylcellulose and carboxymethylcellulose, and lubricants such as talc, stearic acid and stearate salts; and carriers for liquid preparations, such as sucrose, glucose, fructose, invert sugar, sorbitol, xylitol, glycerin, gum arabic, tragacanth and carboxymethylcellulose sodium.

The dosage of the absorption improver upon practice of the method of this invention significantly varies depending on the kind of the absorption improver used. When cilastatin is used as an absorption improver, one of preferred dosages may be about 2–60 mg/day for adults.

The present invention will hereinafter be described in further detail by the following examples. It is, however, to be noted that the present invention is by no means limited to or by the following examples.

EXAMPLE 1

The site of localization of the dipeptidase in the small intestine was determined by the following method. Namely, the small intestine of a rat was fixed under perfusion of the Zamboni's fixative, and paraffin sections were prepared in a manner known per se in the art. Employed as a primary antibody was rabbit antiserum against the dipeptidase purified from the human kidney, as a secondary antibody anti-rabbit IgG goat IgG labeled with the peroxidase, and as a chromogenic substrate 3,3-diaminobenzidine.

As a result, it has been ascertained that the dipeptidase exists in the small intestine of a rat and the site of its localization is the epithelial brush-border membrane (see Photo 1).

EXAMPLE 2

Degradation of penems in epithelial cells isolated from the small intestine of a rat was investigated by the following method. Namely, the epithelial cells were isolated from the small intestine of the rat by the citric acid method reported in The Journal of Biological Chemistry, 248, 2356–2541 (1973).

The epithelial cells so isolated were suspended at 25% w/v in a buffer solution, to which were added 9 µg/ml of sodium (1'R,2"-R,5R,6S)-6-(1'-hydroxyethyl)-2-(2"-tetrahydrofuranyl)penem-3-carboxylate 2.5 hydrate as a penem and 35 µg/ml of cilastatin as a dipeptidase inhibitor. After the resultant solution was incubated at 37° C. for 60 minutes, the free acid of the penem was measured by high performance liquid chromatography (HPLC). The results are shown in Table 1.

TABLE 1

|  | Concentration (µg/ml) |
| --- | --- |
| Added with cilastatin | 7.38 |
| Not added with cilastatin* | 2.08 |

*This means addition of sodium (1'R,2"R,5R,6S)-6-(1'-hydroxyethyl)-2-(2"-tetrahydrofuranyl)penem-3-carboxylate 2.5 hydrate alone.

It is evident that the degradation of the penems carboxylate was inhibited by the addition of cilastatin.

EXAMPLE 3

An improvement in the absorption percentage of the penems in a rat by simultaneous administration of the penems and cilastatin was investigated by the following experiment.

Sodium (1'R,2"R,5R,6S)-6-(1'-hydroxyethyl)-2-(2"-tetrahydrofuranyl)penem-3-carboxylate 2.5 hydrate and cilastatin were mixed at molar ratios in the range of from 1:1 to 2000:1, whereby oral antibacterial compositions were prepared. Those compositions were separately and orally administered to seven-week-old, Sprague-Dawley male rats to give a dose of 57.1 mg (titer)/Kg in terms of the penem carboxylate. The blood was drawn from the femoral artery via a polyethylene catheter over 2.0 hours after the administration. The concentrations of the free acid of the penem in plasma samples were measured by HPLC to determine its highest concentration in plasma and its area under its plasma concentration:time curve (AUC). In addition, the area under the concentration:time curve (AUCpo) of the compound contained in the plasma after its oral administration was compared to the area under the concentration:time curve (AUCiv) when the penemcarboxylate alone was intravenously administered at 10 mg/Kg and, assuming AUCiv be 100%, the percentage of AUCpo was calculated in accordance with the following formula and recorded as Oral Absorption Percentage A.

Oral absorption (%)=AUCpo/AUCiv×11.4/57.1×100

The results are summarized in Table 2

TABLE 2

| Mixing ratio* | Highest concentration in plasma (μg/ml) | AUC (μg · hr/ml) | Absorption (%) |
|---|---|---|---|
| 1:1 | 12.35 | 25.90 | 113.8 |
| 10:1 | 12.67 | 19.59 | 86.3 |
| 100:1 | 8.68 | 21.13 | 93.0 |
| 300:1 | 7.89 | 18.26 | 80.3 |
| 600:1 | 8.08 | 14.93 | 65.6 |
| 1000:1 | 6.89 | 12.22 | 53.7 |
| 2000:1 | 7.69 | 10.94 | 48.1 |
| Single administration | 4.81 | 4.42 | 19.4 |

*"Mixing ratio" means the molar ratio of sodium (1'R,2"R,5R,6S)-6-(1'-hydroxyethyl)-2-(2"-tetrahydrofuranyl)penem-3-carboxylate 2.5 hydrate to cilastatin, whereas "single administration" means administration of sodium (1'R,2"R,5R,6S)-6-(1'-hydroxyethyl)-2-(2"-tetrahydrofuranyl)penem-3-carboxylate 2.5 hydrate alone.

As is apparent from the above results, the oral absorption percentage increased by 2.5 times as much as that available upon single administration of the penem carboxylate by the simultaneous oral administration of cilastatin as little as 1/2000 of the penem carboxylate. An oral absorption percentage as high as 93% was achieved by the simultaneous administration of cilastatin in the amount 1/100 of the penem carboxylate.

EXAMPLE 4

An improvement in the absorption percentage of the penems in dogs by simultaneous administration of the penems and cilastatin was investigated by the following experiment.

Capsules were prepared by filling capsules with a 12.6:1 or 126:1 (by molar ratio) mixture of sodium (1'R,2"-R,5R,6S)-6-(1'-hydroxyethyl)-2-(2"-tetrahydrofuranyl)penem-3-carboxylate 2.5 hydrate and cilastatin, namely, with a powder mixture consisting of 75 mg of the penem carboxylate and 7.5 or 0.75 mg of cilastatin per capsule. One of the capsules was orally administered to matured dogs. The blood was collected during the period of from 0.25 to 4 hours after the administration, and the concentrations of the free acid of the penem in plasma samples were measured by HPLC. Further, urine samples were collected until 24 hours after the administration and the concentrations of the free acid of the penem in the urine samples were measured by HPLC.

The area under the concentration:time curve (AUCpO) of the compound contained in the plasma after its oral administration was compared to the area under the concentration:time curve (AUCiv) when the penemcarboxylate alone was intravenously administered at 10 mg/Kg and, assuming AUCiv be 100%, the percentage of AUCpo was calculated in accordance with the following formula and recorded as oral Absorption Percentage A. Similarly, assuming that the percentage of excretion of the above penemcarboxylate into urine (Uiv) upon its intravenous administration at 10 mg/Kg be 100%, Oral Absorption Percentage B was calculated in accordance with the following formula from the percentage of excretion of the penemcarboxylate into urine upon its oral administration (Upo).

Oral absorption A (%)=AUCpo/AUCiv×10/75×100

Oral absorption B (%)=Upo/Uiv×100

The results are presented in Table 3.

TABLE 3

| | Mixing ratio* | |
|---|---|---|
| | 126:1 | Single administration |
| Highest concentration in plasma (μg/ml) | 26.08 | 11.86 |
| AUC (μg · hr/ml) | 45.57 | 18.62 |
| Oral absorption A (%) | 76.4 | 33.9 |
| Excretion into urine** (%) | 40.32 | 16.58 |
| Oral absorption B (%) | 88.9 | 38.6 |

*"Mixing ratio" means the molar ratio of sodium (1'R,2"R,5R,6S)-6-(1'-hydroxyethyl)-2-(2"-tetrahydrofuranyl)penem-3-carboxylate 2.5 hydrate to cilastatin, whereas "single administration" means administration of sodium (1'R,2"R,5R,6S)-6-(1'-hydroxyethyl)-2-(2"-tetrahydrofuranyl)penem-3-carboxylate 2.5 hydrate alone.
**"Excretion into urine (%)" means the percentage of the penemcarboxylate into urine up to 24 hours after its administration.

As is apparent from the above results, when the penemcarboxylate was orally administered with simultaneous administration of cilastatin in the amount as small as 1/126 of the penemcarboxylate, the oral absorption percentage of the penemcarboxylate was calculated as 76.4% from the area under the concentration:time curve and 88.9% from the percentage of excretion into urine and increased by 2.3 times and 2.3 times as much as those achieved, respectively, when the penemcarboxylate was administered alone.

EXAMPLE 5

Seven-week-old Sprague-Dawley male rats were orally administered with 57.1 mg (titer)/Kg of sodium (1'R,2"R, 5R,6S)-6-(1'-hydroxyethyl)-2-(2"-tetrahydro-furanyl) penem-3-carboxylate 2.5 hydrate. At the same time, cilastatin was orally administered at 7.17, 0.717 or 0.0717 mg/Kg. The blood was collected during the period of from 0.1 to 1.5 hours after the administration. The concentrations of the free acid of the penem in plasma samples were measured by high performance liquid chromatography (HPLC) to determine the highest concentration in plasma and the area under the plasma concentration:time curve (AUC). The results are shown in the following table.

TABLE 4

| Dosage of cilastatin (mg/Kg) | Highest concentration in plasma (μg/ml) | AUC* (μg · hr/ml) |
|---|---|---|
| 7.17 | 12.67 | 19.59 |
| 0.717 | 8.68 | 21.13 |

TABLE 4-continued

| Dosage of cilastatin (mg/Kg) | Highest concentration in plasma (μg/ml) | AUC* (μg · hr/ml) |
| --- | --- | --- |
| 0.0717 | 6.89 | 12.22 |
| 0** | 4.81 | 4.42 |

*Area under the concentration:time curve.
**The value "0" means administration of sodium (1'R,2"R,5R,6S)-6-(1'-hydroxyethyl)-2-(2"-tetrahydrofuranyl)penem-3-carboxylate 2.5 hydrate alone.

At each cilastatin dosage, the area under the plasma concentration:time curve (AUC) upon the oral administration increased by 2.8–4.8 times as much as the AUC obtained upon the single administration of the penemcarboxylate.

Referential Example 1

Seven-week-old Sprague-Dawley male rats were intravenously administered with 11.4 mg (titer)/Kg of sodium (1'R,2'R,5R,6S)-6-(1'-hydroxyethyl)-2-(2'-tetrahydrofuranyl)penem-3-carboxylate 2.5 hydrate. At the same time, cilastatin was orally administered at 7.17, 0.717 or 0.0717 mg/Kg. The blood was collected during the period of from 0.1 to 1.5 hours after the administration. The concentrations of the free acid of the penem in plasma samples were measured by high performance liquid chromatography (HPLC) to determine the area under the plasma concentration:time curve (AUC). The results are presented in the following table.

TABLE 5

| Dosage of cilastatin (mg/Kg) | AUC* (μg · hr/ml) |
| --- | --- |
| 7.17 | 6.74 |
| 0.717 | 5.67 |
| 0.0717 | 6.86 |
| 0** | 7.17 |

*Area under the concentration:time curve.
**The value "0" means administration of sodium (1'R,2"R,5R,6S)-6-(1'-hydroxyethyl)-2-(2"-tetrahydrofuranyl)penem-3-carboxylate 2.5 hydrate alone.

At each cilastatin dosage, the area under the plasma concentration:time curve upon the intravenous administration was not different from that obtained upon the single administration.

EXAMPLE 6

Seven-week-old Sprague-Dawley male rats were orally administered with 57.1 mg (titer)/Kg of sodium (1'R,2"R,5R,6S)-6-(1'-hydroxyethyl)-2-(2"-tetrahydrofuranyl)penem-3-carboxylate 2.5 hydrate. At the same time, glutathione was orally administered at 57.1 or 5.71 mg/Kg. The blood was collected during the period of from 0.1 to 2.0 hours after the administration. The concentrations of the free acid of the penem in plasma samples were measured by high performance liquid chromatography (HPLC) to determine the highest concentration in plasma and the area under the plasma concentration:time curve (AUC). The results are given in the following table.

TABLE 6

| Mixing ratio* | Highest concentration in plasma (μg/ml) | AUC** (μg · hr/ml) |
| --- | --- | --- |
| 1.1:1 | 5.84 | 6.16 |
| 11:1 | 5.03 | 5.54 |
| Single administration | 4.34 | 4.57 |

*"Mixing ratio" means the molar ratio of sodium (1'R,2"R,5R,6S)-6-(1'-hydroxyethyl)-2-(2"-tetrahydrofuranyl)penem-3-carboxylate 2.5 hydrate to glutathione, whereas "single administration" means administration of sodium (1'R,2"R,5R,6S)-6-(1'-hydroxyethyl)-2-(2"-tetrahydrofuranyl)penem-3-carboxylate 2.5 hydrate alone.
**Area under the concentration:time curve.

When glutathione was simultaneously administered in the amount 1/11 of the penem, the area under the plasma concentration:time curve increased by 1.2 times as much as that obtained when the penem was administered alone.

EXAMPLE 7

Sodium (1'R,2"R,5R,6S)-6-(1'-hydroxyethyl)-2-(2"-tetrahydrofuranyl)penem-3-carboxylate 2.5 hydrate and glutathione were mixed to give molar ratios in the range of from 1.1:1 to 110:1. Namely, the penemcarboxylate and glutathione were mixed in amounts of 75 mg (titer) and 75, 15 or 3.75 mg, respectively, per capsule. The resultant mixed powder was filled in a capsule. Capsules were prepared in the manner described above.

One of the capsules was orally administered to matured dogs. The blood was collected during the period of from 0.25 to 4 hours after the administration, and the concentrations of the free acid of the penem in plasma samples and urine samples were measured by HPLC. The results are presented in the following table.

TABLE 7

| Mixing ratio* | Highest concent. in plasma (μg/ml) | AUC** (μg · hr/ml) | Excretion*** into urine (%) |
| --- | --- | --- | --- |
| 1.1:1 | 22.68 | 33.68 | — |
| 11:1 | 18.02 | 25.41 | 20.71 |
| 110:1 | 14.74 | 21.91 | 19.85 |
| Single administration | 11.59 | 17.71 | 16.68 |

*"Mixing ratio" means the molar ratio of sodium (1'R,2"R,5R,6S)-6-(1'-hydroxyethyl)-2-(2"-tetrahydrofuranyl)penem-3-carboxylate 2.5 hydrate to glutathione, whereas "single administration" means administration of sodium (1'R,2"R,5R,6S)-6-(1'-hydroxyethyl)-2-(2"-tetrahydrofuranyl)penem-3-carboxylate 2.5 hydrate alone.
**Area under the concentration:time curve.
***"Excretion in urine (%)" means the excretion of the penemcarboxylate into urine up to 24 hours after the administration.

As is apparent from the above results, by the simultaneous oral administration of glutathione in the amount as small as 1/110 of the penemcarboxylate, its area under the concentration:time curve (AUC) increased by 1.2 times as much as the that obtained upon its single administration.

EXAMPLE 8

Seven-week-old Sprague-Dawley male rats were orally administered with 57.1 mg (titer)/Kg of sodium (1'R,2"R,5R,6S)-6-(1hydroxyethyl)-2-(2"-tetrahydrofuranyl)penem-3-carboxylate 2.5 hydrate. At the same time, N-acetyl-L-cysteine was orally administered at 57.1 mg/Kg. The blood was collected during the period of from 0.1 to 2.0 hours after the administration.

The concentrations of the free acid of the penem in plasma samples were measured by high performance liquid chromatography (HPLC) to determine the highest concentration in plasma and the area under the plasma concentration: time curve (AUC). The results are given in the following table.

TABLE 8

| Mixing ratio* | Highest concentration in plasma (μg/ml) | AUC** (μg · hr/ml) |
|---|---|---|
| 0.6:1 | 6.79 | 5.24 |
| Single administration | 3.29 | 2.52 |

*"Mixing ratio" means the molar ratio of sodium (1'R,2"R,5R,6S)-6-(1'-hydroxyethyl)-2-(2"-tetrahydrofuranyl)penem-3-carboxylate 2.5 hydrate to N-acetyl-L-cysteine, whereas "single administration" means administration of sodium (1'R,2"R,5R,6S)-6-(1'-hydroxyethyl)-2-(2"-tetrahydrofuranyl)penem-3-carboxylate 2.5 hydrate alone.
**Area under the concentration:time curve.

When the penems and N-acetyl-L-cysteine were administered simultaneously, its area under the plasma concentration:time curve increased by 2.1 times as much as that obtained upon the single administration of the penem.

EXAMPLE 9

Capsules:

(Composition)

| | |
|---|---|
| Sodium (1'R,2"R,5R,6S)-6-(1'-hydroxyethyl)-2-(2"-tetrahydro-furanyl)penem-3-carboxylate 2.5 hydrate | 100 mg (titer) |
| Cilastatin | 1 mg |
| Crystalline cellulose | 10 mg |
| Talc | 2 mg |
| Magnesium stearate | 3 mg |

(Procedure)

Using the above composition as ingredients for each capsule, capsules were obtained in a usual manner. Namely, the above ingredients were mixed and the resultant mixture was filled in a capsule to obtain a capsule with the penemcarboxylate and cilastatin filled in the desired amounts.

EXAMPLE 10

Tablets:

(Composition)

| | |
|---|---|
| Sodium (1'R,2"R,5R,6S)-6-(1'-hydroxyethyl)-2-(2"-tetrahydro-furanyl)penem-3-carboxylate 2.5 hydrate | 100 mg (titer) |
| Cilastatin | 3 mg |
| Crystalline cellulose | 10 mg |
| Hydroxypropylcellulose | 4 mg |
| Magnesium stearate | 3 mg |

(Procedure)

Using the above composition as ingredients for each tablet, tablets were obtained in a usual manner. Namely, all the above ingredients other than magnesium stearate were granulated, and magnesium stearate was added to the resulting granules, followed by mixing. The mixture so formed was compressed using a tableting machine, whereby tablets of the desired weight were obtained.

EXAMPLE 11

Dry syrup:

(Composition)

| | |
|---|---|
| Sodium (1'R,2"R,5R,6S)-6-(1'-hydroxyethyl)-2-(2"-tetrahydro-furanyl)penem-3-carboxylate 2.5 hydrate | 100 mg (titer) |
| Cilastatin | 3 mg |
| Sucrose | 550 mg |
| Mannitol | 298 mg |
| Hydroxypropylcellulose | 20 mg |
| Magnesium metasilicate aluminate | 5 mg |

(Procedure)

Using the above composition as ingredients for each gram, a syrup to be dissolved before use was obtained in a usual manner. Namely, all the above ingredients were granulated to obtain a dry syrup containing the penemcarboxylate and cilastatin in the desired amounts.

EXAMPLE 12

Capsules:

(Composition)

| | |
|---|---|
| Sodium (1'R,2"R,5R,6S)-6-(1'-hydroxyethyl)-2-(2"-tetrahydro-furanyl)penem-3-carboxylate 2.5 hydrate | 100 mg (titer) |
| Glutathione | 10 mg |
| Crystalline cellulose | 10 mg |
| Talc | 2 mg |
| Magnesium stearate | 3 mg |

(Procedure)

Using the above composition as ingredients for each capsule, capsules were obtained in a usual manner. Namely, the above ingredients were mixed and the resultant mixture was filled in a capsule to obtain a capsule with the penemcarboxylate and glutathione filled in the desired amounts.

EXAMPLE 13

Tablets:

(Composition)

| | |
|---|---|
| Sodium (1'R,2"R,5R,6S)-6-(1'-hydroxyethyl)-2-(2"-tetrahydro-furanyl)penem-3-carboxylate 2.5 hydrate | 100 mg (titer) |
| Glutathione | 10 mg |
| Crystalline cellulose | 10 mg |
| Hydroxypropylcellulose | 4 mg |
| Magnesium stearate | 3 mg |

(Procedure)

Using the above composition as ingredients for each tablet, tablets were obtained in a usual manner. Namely, all the above ingredients other than magnesium stearate were granulated, and magnesium stearate was added to the resulting granules, followed by mixing. The mixture so formed was compressed using a tableting machine, whereby tablets of the desired weight were obtained.

EXAMPLE 14

Dry syrup:

(Composition)

| Sodium (1'R,2"R,5R,6S)-6-(1'-hydroxyethyl)-2-(2"-tetrahydrofuranyl)penem-3-carboxylate 2.5 hydrate | 100 mg (titer) |
|---|---|
| Glutathione | 10 mg |
| Sucrose | 550 mg |
| Mannitol | 291 mg |
| Hydroxypropylcellulose | 20 mg |
| Magnesium metasilicate aluminate | 5 mg |

(Procedure)

Using the above composition as ingredients for each gram, a syrup to be dissolved before use was obtained in a usual manner. Namely, all the above ingredients were granulated to obtain a dry syrup containing the penemcarboxylate and glutathione in the desired amounts.

EXAMPLE 15

Capsules:

(Composition)

| Sodium (1'R,2"R,5R,6S)-6-(1'-hydroxyethyl)-2-(2"-tetrahydrofuranyl)penem-3-carboxylate 2.5 hydrate | 100 mg (titer) |
|---|---|
| N-Acetyl-L-cysteine | 10 mg |
| Crystalline cellulose | 10 mg |
| Talc | 2 mg |
| Magnesium stearate | 3 mg |

(Procedure)

Using the above composition as ingredients for each capsule, capsules were obtained in a usual manner. Namely, The above ingredients were mixed and the resultant mixture was filled in a capsule to obtain a capsule with the penemcarboxylate and N-acetyl-L-cysteine filled in the desired amounts.

EXAMPLE 16

Tablets:

(Composition)

| Sodium (1'R,2"R,5R,6S)-6-(1'-hydroxyethyl)-2-(2"-tetrahydrofuranyl)penem-3-carboxylate 2.5 hydrate | 100 mg (titer) |
|---|---|
| N-Acetyl-L-cysteine | 10 mg |
| Crystalline cellulose | 10 mg |
| Hydroxypropylcellulose | 4 mg |
| Magnesium stearate | 3 mg |

(Procedure)

Using the above composition as ingredients for each tablet, tablets were obtained in a usual manner. Namely, all the above ingredients other than magnesium stearate were granulated, and magnesium stearate was added to the resulting granules, followed by mixing. The mixture so formed was compressed using a tableting machine, whereby tablets of the desired weight were obtained.

EXAMPLE 17

Dry syrup:

(Composition)

| Sodium (1'R,2"R,5R,6S)-6-(1'-hydroxyethyl)-2-(2"-tetrahydrofuranyl)penem-3-carboxylate 2.5 hydrate | 100 mg (titer) |
|---|---|
| N-Acetyl-L-cysteine | 10 mg |
| Sucrose | 550 mg |
| Mannitol | 291 mg |
| Hydroxypropylcellulose | 20 mg |
| Magnesium metasilicate aluminate | 5 mg |

(Procedure)

Using the above composition as ingredients for each gram, a syrup to be dissolved before use was obtained in a usual manner. Namely, all the above ingredients were granulated to obtain a dry syrup containing the penemcarboxylate and N-acetyl-L-cysteine in the desired amounts.

We claim:

1. A method for the improvement of the gastrointestinal absorption of a penem or carbapenem antibiotic, which comprises orally co-administering the said antibiotic and an absorption improver selected from substances capable of inhibiting the dipeptidase localized on/in epithelial cells of the small intestine, cilastatin, glutathione and N-acetyl-L-cysteine.

2. A method of preparing a penem or carbapenem antibiotic, comprising:

combining a penem or carbapenem antibiotic with a gastrointestinal absorption improver which is a member selected from the group consisting of (i) substances capable of inhibiting the dipeptidase localized on/in epithelial cells of the small intestine, (ii) cilastatin, (iii) glutathione and (iv) N-acetyl-L-cysteine, wherein the molar ratios of said antibiotic to said substances and said antibiotic to cilastatin each range from about 10:1 to about 300:1, the molar ratio of said antibiotic to said glutathione ranges from about 1:3 to about 110:1, and the molar ratio of said antibiotic to N-acetyl-L-cysteine ranges from about 1:3 to about 60:1, thereby preparing an orally administrable antibiotic composition.

3. A method for improving the gastrointestinal absorption of a penem or carbapenem antibiotic, which comprises:

orally co-administering the said antibiotic and N-acetyl-L-cysteine as a gastrointestinal absorption improver to a subject.

4. A method of preparing a penem or carbapenem antibiotic, comprising:

combining a penem or carbapenem antibiotic with N-acetyl-L-cysteine as an absorption improver, wherein the mole ratio of said antibiotic to N-acetyl-L-cysteine ranges from about 1:3 to about 60:1, thereby preparing an orally administrable antibiotic composition.

5. A method of preparing a penem or carbapenem antibiotic, comprising:

combining a penem or carbapenem antibiotic with a gastrointestinal absorption improver which is a member selected from the group consisting of (i) substances capable of inhibiting the dipeptidase localized on/in epithelial cells of the small intestine, (ii) cilastatin, (iii)

glutathione and (iv) N-acetyl-L-cysteine, wherein the molar ratio of said antibiotic to cilastatin ranges from about 10:1 to about 300:1, the molar ratio of said antibiotic to said glutathione ranges from about 1:3 to about 110:1, and the molar ratio of said antibiotic to N-acetyl-L-cysteine ranges from about 1:3 to about 60:1, thereby preparing an orally administrable antibiotic composition.

* * * * *